United States Patent [19]

Premachandra

[11] 3,970,746

[45] July 20, 1976

[54] IMMUNOASSAY FOR THE MEASUREMENT OF TOTAL THYROXINE IN BLOOD SERUM

[75] Inventor: Bhartur Premachandra, 5 Blaytonn Lane, La Due, Mo. 63124

[73] Assignee: Bhartur Premachandra, La Due, Mo.

[22] Filed: Sept. 5, 1974

[21] Appl. No.: 503,230

[52] U.S. Cl. .............................. 424/1.5; 23/230 B; 23/230.6
[51] Int. Cl.² ...................... G01N 31/00; G01T 1/16
[58] Field of Search ...................... 23/230 B; 424/1

[56] References Cited
UNITED STATES PATENTS
3,206,602  9/1965  Eberle ................................ 250/364

OTHER PUBLICATIONS

Murphy et al., Journal of Clinical Endocrinology, vol. 24, Feb., 1964, pp. 187–196.

Mitchell et al., Journal of Clinical Endoerinology, vol. 20, Nov. 1960, pp. 1474–1483.

Sterling et al., Journal of Clinical Endocrinology, vol. 21, Apr. 1961, pp. 456–464.

*Primary Examiner*—Leland A. Sebastian
*Assistant Examiner*—Christine M. Nucker
*Attorney, Agent, or Firm*—Gildo E. Fato; Robert L. Niblack

[57] ABSTRACT

An immunoassay for the measurement of total thyroxine in blood serum which employs trichloracetic acid and base to precipitate or denature the protein to quantitatively extract thyroxine. This procedure along with the use of radioactively labeled $T_4$ antiserum, and the resin sponge to separate free and bound hormone, minimizes the number of steps required in the assay, which can be performed in the same tube in less than ninety minutes.

5 Claims, No Drawings

IMMUNOASSAY FOR THE MEASUREMENT OF TOTAL THYROXINE IN BLOOD SERUM

BACKGROUND OF THE INVENTION

The measurement of total serum thyroxine (T4) is used to help diagnose thyroid condition and evaluate therapy. The assay is performed in vitro thereby avoiding administration of radioactivity to the patient. Only a blood sample of the patient is required. The T4 assay, employing a radioactive isotope, permits evaluation of thyroid function under certain circumstances in which other standard methods such as the measurement of protein bound iodine may not be applicable due to the presence of various forms of iodine. Radioimmunoassay T4 procedures may be used following administration of iodine containing compounds and can also be used during the course of treatment with thyroid medication (in general more specific than other tests). The measurement of total serum thyroxine offers a means for measuring the direct output of the thyroid gland as thyroxine.

T4 assays require a means for extracting T4 from plasma proteins (alcholic solvents are extensively used for this purpose) and a method for separation of free and bound hormone for which charcoal, double antibody techniques, etc. are used. Such steps are cumbersome, exacting and time consuming.

SUMMARY OF THE INVENTION

The method of the present invention comprises a simple, accurate and rapid radioimmunoassay for the measurement of serum total thyroxine in which trichloracetic acid is used to precipitate the protein and a base such as sodium hydroxide to dissolve it. The acid and base can be used in separate steps or combined in mixture and are used in place of other materials, such as alcohol for the extraction of the protein. One hundred percent extraction is obtained and consequently no correction is required.

The procedure provides simplicity since no centrifugation, evaporation, sample or reagent transfers, column preparation, or weighing of reagents is required. Further, all of the assay steps can be carried out in the same tube. Since none of the noted cumbersome steps are required in performing the assay with the present invention, rapidity of performing the assay is facilitated. The assay does not require correction for thyroxine extraction recovery and has good specificity in that drugs that affect or have the potential to affect competitive protein binding or other procedures have no effect. Because of the fewer number of reagents in smaller amounts are required, the procedure is economical and is applicable in routine use in humans and animals and is especially useful in pediatrics and small animal research because of the micro amounts of test sera required to perform the assay.

DETAILED DESCRIPTION

The materials and reagents required for conducting the described radioimmunoassay are prepared as follows.

T4 antibodies were generated in rabbits immunized against bovine thyroglobulin (1%) emulsified in Freund's adjuvant once weekly for 3 weeks. Animals were bled generally eight weeks after primary immunization. The potency of the antiserum was such that the antibodies bound approximately 60% of the tracer dose of $^{125}I$—T4 (equivalent to 2 $\mu$g/100 ml). The dilution of the antiserum (1/20) for the assay was carried out as follows: To 25 ml. antiserum, 15 ml. propylene glycol and 5 ml. phenol (1%) were added and the resulting solution was made up to 500 ml. with phosphate buffer (1 M, pH 7.4). Prior to dilution, antiserum was labeled with $^{125}I$—T4 (.5 $\mu$g $^{125}I$—T4/25 ml. antiserum).

$^{125}I$—T4

Commercially available thyroxine labeled with $^{125}I$ was employed. The labeled material had a specific activity of about 60 $\mu c/\mu g$ and was supplied in 50% propylene glycol.

T4 Standards

Reagent grade thyroxine (free acid) was used. After overnight drying at 40°C., appropriate amounts were weighed, dissolved in minimum amount of 0.1 N NaOH, and the standard solutions were prepared in 0.25% albumin.

Serum Free Thyronine

T4 standards were made in thyronine free human serum which was prepared by the addition of 20 grams of activated charcoal to 100 ml. of pooled normal human serum. The slurry was stirred slowly for 1 hour at room temperature and left in the cold room (40° – 50°F) for 24 hours after which it was centrifuged 3 to 5 times and subjected to serial filtration through Millipore filters.

The radioimmunoassay of the present invention is conducted in the following manner.

Procedure

25 $\mu$l of serum are pipetted into tubes followed by the addition of 0.1 ml. of 30% trichloroacetic acid (TCA) to precipitate plasma proteins. After shaking the tubes for 5 minutes, 0.3 ml. of 0.75 N sodium hydroxide is then added to solubilize thyroxine liberated from native T4binding proteins. A TCA—NaOH mixture is just as satisfactory as separate additions of TCA and NaOH, thereby simplifying the procedure by yet another step. After five minute agitation of the tubes, 0.6 ml. of $^{125}I$—T4 labeled thyroxine binding rabbit antibovine thyroglobulin serum (1/20, pH 7.4) is added followed by further five minute shaking. After 15 minute equilibration at room temperature, the tubes are placed in an ice bath (2°-4°C.) for an additional 15 minute period. An anionic resin sponge is then introduced into each tube and squeezed with a plunger. The radioactivity in a few tubes is counted to represent initial activity. After one hour incubation with reactants, the sponges are washed with deionized water four times and the radioactivity determined (final activity). The sponge uptake of radioactivity (final activity/initial activity X 100, measured of $^{125}I$—T4 displacement from antiserum) is linearly related to thyroxine present in standard or test serum (up to 20 $\mu$g T4/100 ml. serum or more depending on choice and dilution of T4 binding antisera).

T4 Calibration Line (standard curve), Precision and Sensitivity

T4 Calibration

When percent sponge $^{125}I$—T4 uptake at various T4 levels is plotted, a linear response is obtained. With appropriate dilution of antiserum and the adjustment of the volume of the reactants, a linear response could be obtained even when the volume of the test serum employed was 0.1 ml. The linear sponge $^{125}I$—T4 uptake response throughout the range of T4 standards tested (0 – 20 $\mu$g T4/100 ml. serum) indicates that the assay sensitivity is uniform throughout the measuring range unlike in curvilinear responses where assay sensitivity is compromised at high T4 values.

Assay Precision

The precision of the assay was determined in two ways:

Intra-assay precision

For intra-assay precision coefficient of variances between the replicates in three serum samples with high, medium and low T4 concentration were computed and are shown below:

|  | No. of Determinations | Mean ($\mu$g/100 ml.) | Std. Deviation | Coefficient of Variance % |
| --- | --- | --- | --- | --- |
| Serum with low T4 value | 20 | 5.0 | .29 | 5.8 |
| Serum with median normal T4 value | 20 | 7.5 | .72 | 9.6 |
| Serum with high T4 value | 18 | 14.6 | .80 | 5.5 |

Inter-assay precision

For inter-assay precision, the coefficient of variance was computed between replicates determined in successive assays using different batches of reagents including fresh labelling of aliquots of frozen immune sera. The results are shown below:

|  | No. of Determinations | Mean ($\mu$g/100 ml.) | Std. Deviation | Coefficient of Variance % |
| --- | --- | --- | --- | --- |
| Pooled Normal human serum | 15 | 7.3 | .86 | 11.8 |

Sensitivity

The lower limit of the sensitivity of the technique was 0.8 $\mu$g/100 ml. The sensitivity was determined by testing equal increments of 0.2 $\mu$g T4 (/100 ml.) starting from 0.2 $\mu$g T4 and on up to 1 $\mu$g T4/100 ml. The lowest T4 concentration at which a change in sponge uptake response could be detected with precision was construed as the lower sensitivity limit of the assay. While greater sensitivity (i.e. change in sponge uptake for a given increment of T4) particularly at the lower part of the calibration line (hypothyroid range) could be easily obtained by the manipulation of antiserum dilution, no particular advantage was noted insofar as separation of T4 values in various thyroid states were concerned and furthermore, a curvilinear relationship was noted with extreme sensitivity, i.e., at higher T4 levels (sponge uptake) response differentials were not great.

Specificity

For evaulating specificity of the assay, T4 values were determined in pooled normal human serum prior to and after addition of various substances. The amounts and types of compounds tested are shown in Table 1. It is apparent from the table that excepting high levels of T3 (and such levels far exceed even therapeutic doses) none of the substances tested had any effect on the assay. Such a high degree of specificity is particularly important when compared with the types of substances tested, some of which have been shown to influence T4 values in previous competitive protein binding analysis techniques. The various antidiabetic drugs, salicylates, anticoagulants, organic and inorganic dyes, radioopaque materials did not affect the assay, nor did dilantin in a dose of 500 $\mu$g/ml. Complement which has been shown to interfere in the double antibody separation technique was without effect on the assay probably because of its (complement) denaturation in the presence of TCA—NaOH. The lack of effect of glucose showed that the technique also was not affected by osmolality changes. Of particular interest was the failure of immunoglobulins to influence the assay. The importance lies not only in the freedom from interference of the assay by antibodies (antithyroglobulin itself) but also in the demonstration that the assay is not readily influenced by variations in protein concentration.

Table I

Specificity of Thyroxine Immunoassay

| Substances Added to Pooled Human Serum | Amount Added per ml. | T4 ($\mu$g/100 ml.) |
| --- | --- | --- |
| — | 0 | 7.2 ± 0.5 |
| Arthropan | 500 $\mu$g | 7.7 |
| Iodoacetamide | 100 $\mu$g | 6.8 |
| Sodium Iodide | 100 $\mu$g | 6.3 |
| Phenoformin Hol | 50 $\mu$g | 6.7 |
| Tolinase | 50 $\mu$g | 6.7 |
| Heparin | 1000 units | 6.8 |
| Dilantin | 500 $\mu$g | 7.9 |
| 3-iodo-l-tyrosine | 50 $\mu$g | 7.2 |
| Immune serum glob.(human) | 50 $\mu$g | 7.3 |
| Goat antiserum to human TG. | .1 mg | 7.3 |
| Glucose | 100 $\mu$g | 6.3 |
| 3,3,5 triiodo-1-thyronine | 100 $\mu$g | >80 |
| Hypaque | 6000 $\mu$g | 7.0 |
| Phenylbutazone | 100 $\mu$g | 7.3 |

In the procedure of the present invention, some means of separating the unbound $I^{125}$ thyroxine from that which is bound to the thyroxine antibody is required. A convenient means for separation is an ion exchange resin. The resin can be in the form of granules but since centrifugation is required if the granules are used, it is preferred to employ a resin sponge comprising particles of ion exchange resin dispersed within a plastic sponge material. In its preferred embodiment, an anionic resin-sponge is employed to separate the unbound $I^{125}$ thyroxine from the bound thyroxine. When the percent uptake of the sponge is compared with a standard curve, the quantity of thyroxine present in the patient's serum can be determined.

The resin sponge employed in this invention comprises a polyurethane foam of intercommunicating cell type containing a strong base anion-exchange resin as described in U.S. Pat. Nos. 3,024,207 and 3,094,494. Such a urethane foam resin may be prepared by incorporating the ion-exchange resin particles in a mixture of a polyether or polyester and a polyisocyanate and then subjecting the mixture to the usual conditions for producing foams of the polyurethane type. An example of a suitable ion-exchange resin is a strongly basic anion-exchange resin, chloride form, such as that marketed under the trademark Amberlite IRA400. Such resins can be prepared by the process disclosed in U.S. Pat. No. 2,591,573. The resin which is utilized should not remove ions already bound to the globulin molecule nor bind the whole molecule.

The resin sponge can be made in various forms. A convenient embodiment is a cylindrical plug which can be easily placed in the bottom of a container adapted for placement in the well of conventional scintillation counters. The actual dimensions of the cylindrical plug of resin sponge will be determined by the volume of serum employed in the test and by the size of the container utilized to hold the serum and the radioactive solution. It is desirable that a plug of standard size and a standard volume of serum be established in utilizing the method of the present invention. Various modifications can be made in the type of resin and the content thereof in the polyurethane foam or in the makeup and characteristics of the sponge. Modifications can also be made in the volume of serum and amount of tracer material employed in the method. Such variations will not detract from the operability of the method. To obtain the greatest advantage from the practice of the method, a selected volume of serum and a selected size of a particular resin sponge should be adapted as standards.

In conducting the radioimmunoassay of the present invention, use of trichloroacetic acid of too high a concentration will result in destruction of the protein. A concentration of less than 40% solution of trichloroacetic acid is therefore preferred.

What is claimed is:

1. A radioimmunoassay for the measurement of total thyroxine in a serum sample which comprises the steps of:
   mixing trichloroacetic acid and sodium hydroxide with the serum sample to form a mixture;
   adding radioactively labeled thyroxine antiserum to the mixture;
   permitting the mixture to equilibrate;
   placing in contact with the mixture a resin sponge comprising a polyurethane foam of intercommunicating cell type containing a strong base anion exchange resin;
   incubating the mixture and resin sponge;
   measuring the initial radioactivity of the combined mixture and resin sponge with suitable detecting means;
   removing the resin sponge from the mixture;
   washing the resin sponge; and
   measuring the residual radioactivity in the resin sponge.

2. The radioimmunoassay of claim 1 in which thyroxine antiserum labeled with $^{125}I-T_4$ is allowed to react with $T_4$ present in serum and in the presence of $T_4$ extracting solvent (acid-base mix).

3. The radioimmunoassay of claim 2 in which the mixture and resin sponge is incubated for about 1 hour.

4. The radioimmunoassay of claim 3 in which the trichloroacetic acid has a concentration of less than 40%.

5. The radioimmunoassay of claim 4 in which 0.1 milliliter of a 30% solution of trichloroacetic acid and 0.3 milliliter of an 0.75 normal solution of sodium hydroxide is added to 25 microliters of the serum sample.

* * * * *